United States Patent
Kasahara et al.

(10) Patent No.: US 7,418,291 B2
(45) Date of Patent: Aug. 26, 2008

(54) BODY FAT MEASURING DEVICE

(75) Inventors: Yasuhiro Kasahara, Tokyo (JP); Takashi Shiokawa, Tokyo (JP)

(73) Assignee: Tanita Corporation, Tokyo (JP)

( * ) Notice: Subject to any disclaimer, the term of this patent is extended or adjusted under 35 U.S.C. 154(b) by 166 days.

(21) Appl. No.: 11/000,998

(22) Filed: Dec. 2, 2004

(65) Prior Publication Data

US 2005/0124909 A1 Jun. 9, 2005

(30) Foreign Application Priority Data

| Dec. 5, 2003 | (JP) | ............................. 2003-407517 |
| Jun. 25, 2004 | (JP) | ............................. 2004-187869 |

(51) Int. Cl.
- *A61B 5/05* (2006.01)
- *A61B 5/103* (2006.01)
- *A61B 5/117* (2006.01)

(52) U.S. Cl. ...................................... 600/547; 600/587

(58) Field of Classification Search ................. 600/372, 600/382, 393, 547, 587; 119/174; 324/692
See application file for complete search history.

(56) References Cited

U.S. PATENT DOCUMENTS

| 5,372,141 | A | * | 12/1994 | Gallup et al. | ............... | 600/547 |
| 5,720,296 | A | * | 2/1998 | Cha | ............... | 600/554 |
| 6,487,445 | B1 | * | 11/2002 | Serita et al. | ............... | 600/547 |
| 6,850,798 | B2 | * | 2/2005 | Morgan et al. | ............... | 600/547 |
| 2003/0149375 | A1 | | 8/2003 | Chen | | |

FOREIGN PATENT DOCUMENTS

| EP | 1 092 388 A1 | 4/2001 |
| EP | 1 203 562 A2 | 5/2002 |
| EP | 1 452 132 A2 | 1/2004 |
| JP | 2003-144005 | 5/2003 |

OTHER PUBLICATIONS

European Search Report for Corresponding Application EP 04027560.4

* cited by examiner

*Primary Examiner*—Max Hindenburg
*Assistant Examiner*—Michael Apanius
(74) *Attorney, Agent, or Firm*—McDermott Will & Emery LLP

(57) ABSTRACT

Disclosed is a device for measuring body fat of an animal. Embodiments include an input unit for entering individual information of the animal, a bioelectric impedance input unit for measuring the bioelectric impedance of the animal, and a morphological measurement value input unit for entering morphological measurement values for the girth and length of the body of the animal. An impedance-based calculation unit calculates a body fat rate based on the bioelectric impedance, and a morphological measurement value-based calculation unit calculates the body fat rate based on the morphological measurement values. A calculation switching unit checks to determine whether the resulting bioelectric impedance is proper, and automatically switches between the impedance-based calculation unit and the morphological measurement value-based calculation unit depending on the result of the determination.

6 Claims, 9 Drawing Sheets

BODY FAT MEASURING DEVICE

BACKGROUND OF THE INVENTION

1. Field of the Invention

The present invention relates to a body fat measuring device for measuring the body fat of an animal using a plurality of measuring means which are successively put into operation by switching therebetween.

2. Prior Art

There has been developed a body fat measuring device for an animal using noninvasive impedance measurement in which a dog is suspended by a fixing tool in such manner that the dog is restricted in posture while standing on all four limbs, but spaced away from the floor. A measurement person wears a set of gloves on both hands each having an impedance measurement electrode affixed on the palm portion thereof, and grasps the front and rear limbs of the dog at the specific positions so that the electrodes on the gloves are contact therewith for measuring the impedance between the specific positions on the front and rear limbs of the dog. Then, the body fat of the dog is calculated based on the impedance measured (see Patent Document 1).

Patent Document 1: Japanese Patent Laid-Open No. 2003-144005.

However, the body fat measuring device in the prior art using impedance measurement, as described above, is defective in that because of necessity of grasping the limbs of the animal at the specific positions the measurement person needs to have some expert knowledge about bone and muscle structure of the animal. As the result, there was such tendency that the electrodes are likely to be shifted in position to produce an erroneous measurement depending on the manner that the limbs are grasped. In addition, it was sometimes difficult to conduct the measurement due to effect of body hair of the animal on the contact point with the electrode, violent action of the animal, etc.

In view of the above an object of the present invention is to provide a body fat measuring device for measuring the body fat of an animal under test using the most suitable measuring means for the animal under test selected from among a plurality of measuring means by switching therebetween depending on behavior of the animal under test and contact condition of electrodes.

SUMMARY OF THE INVENTION

To attain such object the present invention provides a body fat measuring device for measuring body fat of an animal, comprising: an individual information input unit; a bioelectric impedance input unit; a morphological measurement value input unit; an impedance-based calculation unit; a morphological measurement value-based calculation unit; and a calculation switching unit, wherein said individual information input unit enters the individual information of the animal, said bioelectric impedance input unit measures and enters the bioelectric impedance of the animal, said morphological measurement value input unit enters the morphological measurement values for the girth of body and the length of body of the animal, said impedance-based calculation unit calculates the body fat rate based on the bioelectric impedance, said morphological measurement value-based calculation unit calculates the body fat rate based on the morphological measurement values for the girth of body and the length of body of the animal, and said calculation switching unit checks to determine whether the resulting bioelectric impedance is proper or not and then automatically switches between said impedance-based calculation unit and said morphological measurement value-based calculation unit depending on the result of determination.

According to one embodiment of the present invention said bioelectric impedance input unit includes at least one of a set of trunk portion electrodes and a set of sole electrodes, wherein said set of trunk portion electrodes is contact with the trunk portion and said set of sole electrodes is contact with the soles of limbs of the animal.

According to another embodiment of the present invention said bioelectric impedance input unit includes both a set of trunk portion electrodes and a set of sole electrodes, wherein said set of trunk portion electrodes is contact with the trunk portion and said set of sole electrodes is contact with the soles of limbs of the animal, and said bioelectric impedance input unit further includes a electrode switching unit to automatically switch between the set of trunk portion electrodes and the set of sole electrodes.

According to further embodiment of the present invention said bioelectric impedance input unit further includes an auxiliary unit by which each of soles of four limbs of the animal is likely to make contact with each of the associated sole electrodes.

According to yet further embodiment of the present invention the device further comprises a base, a platform disposed on the base, on which the animal lies on one's belly while floating the four limbs of the animal in the air, and a front limb auxiliary support and a rear limb auxiliary support both of which are drawn from the platform to such positions that they become contact to the roots of the front and rear limbs of the animal for supporting the trunk portion thereof, said bioelectric impedance input unit includes a set of trunk portion electrodes provided at both end portions of the front limb auxiliary support and the rear limb auxiliary support for making contact with the trunk portion of the animal, and a set of sole electrodes provided on the base for making contact with soles of four limbs of the animal, and the device further comprises a switching unit which acts to automatically switch between the set of trunk portion electrodes and the set of sole electrodes.

According to yet further embodiment of the present invention the platform is supported on a height-adjustable lift unit provided on the base.

According to yet further embodiment of the present invention said morphological measurement value input unit includes an operation unit provided on the base.

According to yet further embodiment of the present invention said morphological measurement value input unit includes a distance-between-limbs measurement unit which measures the distance between front and rear limbs, i.e. the body length of the animal, based on the distance over which the front limb auxiliary support and the rear limb auxiliary support are moved relative to the platform.

According to yet further embodiment of the present invention said morphological measurement value input unit includes a weight measuring unit provided on the base.

According to yet further embodiment of the present invention said morphological measurement value input unit includes a measuring tool with an automatic distance measuring encoder included in the front limb auxiliary supports for measuring girth of the animal.

EFFECTS OF THE INVENTION

A body fat measuring device for measuring body fat of an animal according to the present invention comprises: an individual information input unit; a bioelectric impedance input unit; a morphological measurement value input unit; an impedance-based calculation unit; a morphological measurement value-based calculation unit; and a calculation switching unit, wherein said individual information input unit enters the individual information of the animal, said bioelectric impedance input unit measures and enters the bioelectric impedance of the animal, said morphological measurement value input unit enters the morphological measurement values for the girth of body and the length of body of the animal, said impedance-based calculation unit calculates the body fat rate based on the bioelectric impedance, said morphological measurement value-based calculation unit calculates the body fat rate based on the morphological measurement values for the girth of body and the length of body of the animal, and said calculation switching unit checks to determine whether the resulting bioelectric impedance is proper or not and then automatically switches between said impedance-based calculation unit and said morphological measurement value-based calculation unit depending on the result of determination. Accordingly, even in such case that there is no impedance value resulted because of any movement of the animal or significant effect of body hair of the animal then calculation of body fat rate can still be done by morphological measurement.

The bioelectric impedance input unit may include at least one of a set of trunk portion electrodes and a set of sole electrodes, wherein the set of trunk portion electrodes is contact with the trunk portion and the set of sole electrodes is contact with the soles of limbs of the animal. Accordingly, any person can noninvasively measure the impedance of the trunk portion of the animal without any need to have some expert knowledge about living body structure of the animal.

The bioelectric impedance input unit may include both a set of trunk portion electrodes and a set of sole electrodes, wherein the set of trunk portion electrodes is contact with the trunk portion and the set of sole electrodes is contact with the soles of limbs of the animal, and the bioelectric impedance input unit may further include a electrode switching unit to automatically switch between the set of trunk portion electrodes and the set of sole electrodes. Accordingly, the impedance measurement for any of various types of animals can be done using the most suitable type of electrodes selected from among said sets of electrodes by switching therebetween.

BRIEF DESCRIPTION OF THE DRAWINGS

The present invention will be described in more detail with reference to the accompanying drawings, in which.

BEST MODE FOR IMPLEMENTING THE INVENTION

Figure 1:
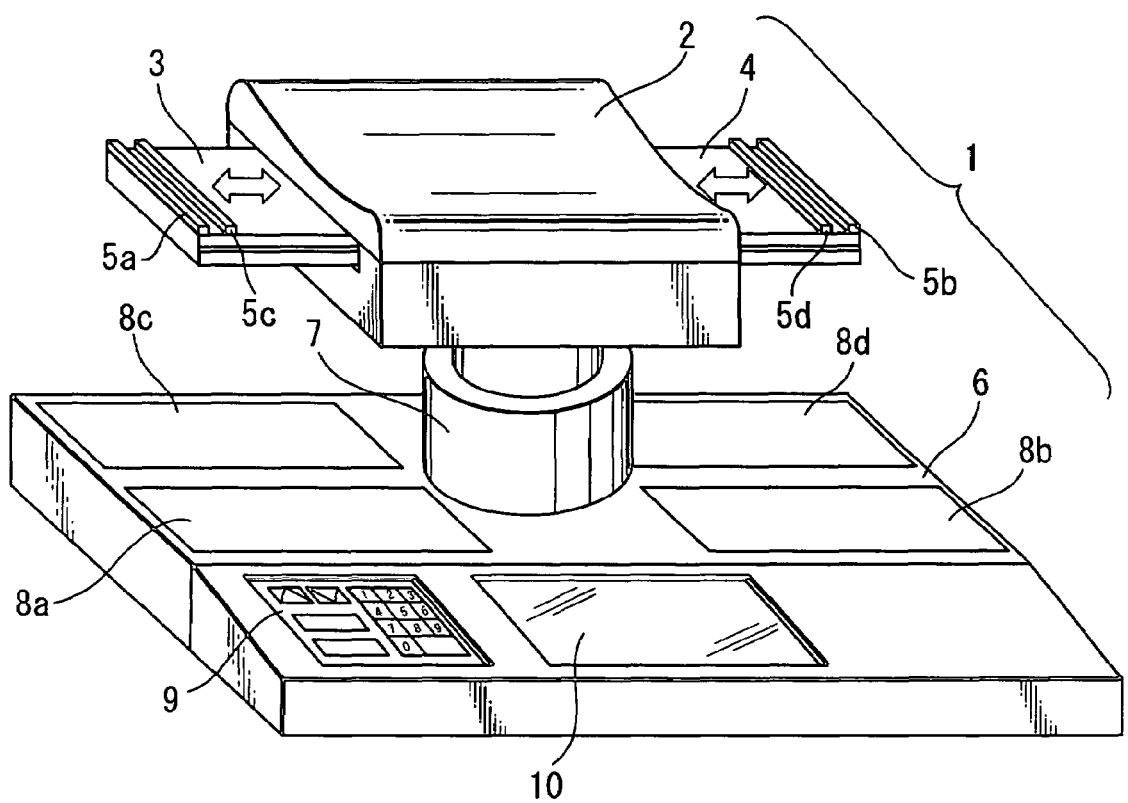
FIG. 1 is a perspective view illustrating external appearance of a measuring device according to first embodiment of the present invention.

The present invention provides a body fat measuring device for measuring body fat of an animal comprising: an individual information input unit; a bioelectric impedance input unit; a morphological measurement value input unit; an impedance-based calculation unit; a morphological measurement value-based calculation unit; and a calculation switching unit, wherein said individual information input unit enters the individual information of the animal, said bioelectric impedance input unit measures and enters the bioelectric impedance of the animal, said morphological measurement value input unit enters the morphological measurement values for the girth of body and the length of body of the animal, said impedance-based calculation unit calculates the body fat rate based on the bioelectric impedance, said morphological measurement value-based calculation unit calculates the body fat rate based on the morphological measurement values for the girth of body and the length of body of the animal, and said calculation switching unit checks to determine whether the resulting bioelectric impedance is proper or not and then automatically switches between said impedance-based calculation unit and said morphological measurement value-based calculation unit depending on the result of determination. Furthermore, the bioelectric impedance input unit includes at least one of a set of trunk portion electrodes and a set of sole electrodes, wherein the set of trunk portion electrodes is contact with the trunk portion and the set of sole electrodes is contact with the soles of limbs of the animal. Alternatively, the bioelectric impedance input unit may include both a set of trunk portion electrodes and a set of sole electrodes, but in such case, it also includes an electrode switching unit to automatically switch between the set of trunk portion electrodes and the set of sole electrodes.

Description of First Embodiments

A device according to first embodiment of the present invention is configured to derive the body fat rate of an animal under test by any one of the following three types of measurement processes, which are successively performed by switching therebetween:

First impedance measurement process in which an animal under test is fixed by a fixing tool with measurement electrodes contact with the trunk portion of the animal for measuring the impedance thereof;

Second impedance measurement process in which the measuring electrodes are contact with the soles of four limbs of the animal for measuring the impedance thereof, the first and second impedance measurement processes each produces impedance value used for calculation of body fat rate of the animal; and Third process in which the body fat rate is calculated based on the morphological measurement value.

The highest precision with which the body fat rate is measured is resulted from the first impedance measurement process because of measurement of trunk portion impedance directly performed on the trunk portion of the animal. The next higher precision is resulted from the second impedance measurement process in which the impedance substantially equal to that of the trunk portion is measured by canceling the four limbs impedance according to prior art four-electrode impedance measurement method. The lowest precision is resulted from the third process in which the body fat rate is calculated based on the morphological measurement value. The device of the present invention is configured to automatically judge behavior of the animal or contact condition of the impedance measurement electrodes to select which one is most suitable for that animal from among those measurement processes, beginning with one having highest precision in measurement.

Figure 2:
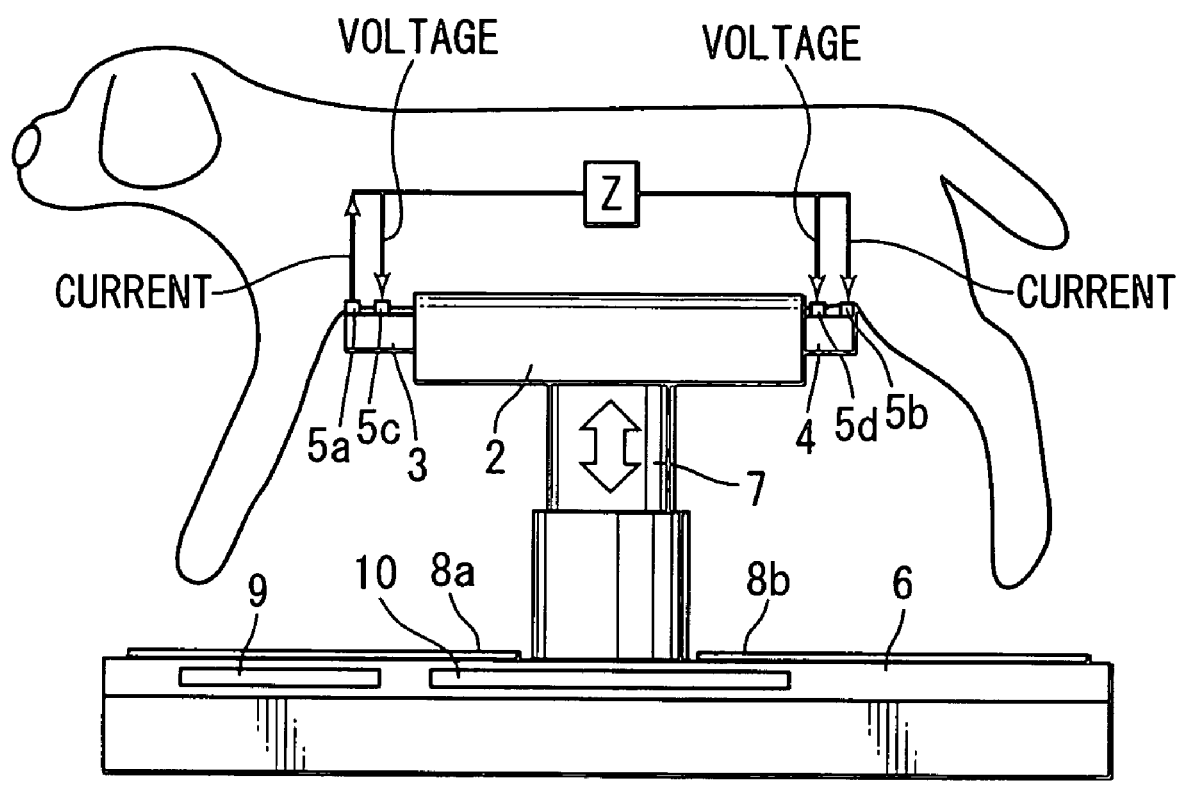
FIG. 2 is a side view illustrating the measuring device at the time when the measuring is being done, and also illustrating the principle of measurement.
Figure 3:
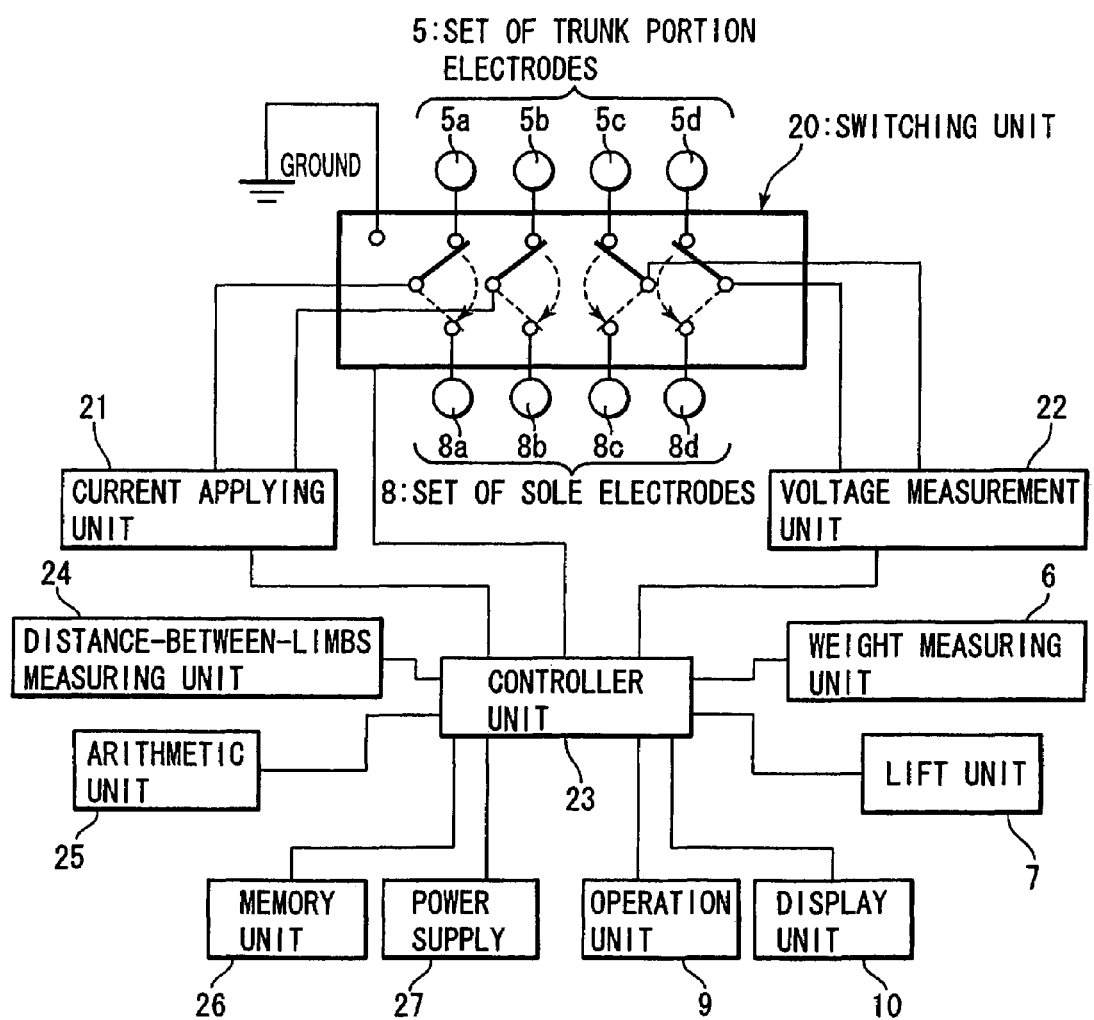
FIG. 3 is an electrical block diagram of the measuring device.

The device for measuring the body fat of an animal according to this first embodiment will be described in more detail with reference to FIGS. 1 to 3. In particular, FIG. 1 is a perspective view illustrating external appearance of the measuring device of the present invention; FIG. 2 is a side view illustrating the measuring device at the time when the measuring is being done, and also illustrating the principle of measurement; and FIG. 3 is an electrical block diagram of the measuring device.

Referring to FIGS. 1 and 2, an external construction of the measuring device 1 for measuring the body fat of an animal according to the present invention will be described. The measuring device 1 includes a platform 2 on which the animal lies on its belly while floating the four limbs of the animal in the air. The measuring device 1 further includes a front limb auxiliary support 3 and a rear limb auxiliary support 4 which can be drawn from the platform 2 to contact the roots of the front and rear limbs of the animal to accept any difference in size of the animal, and which can assist supporting the body portion from the roots of the front limbs to that of the rear limbs (hereafter referred to as a "trunk portion") of the animal.

The front limb auxiliary support 3 and the rear limb auxiliary support 4 have a set of trunk portion electrodes 5 consisting of impedance measurement electrodes 5a, 5b, 5c and 5d provided at both end portions thereof for making contact with the trunk portion of the animal. In particular, a current applying electrode 5a is provided at an end portion of the front limb auxiliary support 3 and a voltage measurement electrode 5c is provided at the position inside relative to the current applying electrode 5a. In the same manner, a current applying electrode 5b is provided at an end portion of the rear limb auxiliary support 4 and a voltage measurement electrode 5d is provided at the position inside relative to the current applying electrode 5b.

Although not shown in the figures, the platform 2 and the front and rear limb auxiliary supports 3 and 4 each comprise a prior art slide mechanism, a stopper mechanism capable of arbitrary or gradually positioning the front and rear limb auxiliary supports 3 and 4, and a prior art encoder for measuring the distance in movement of the front and rear limb auxiliary supports 3 and 4.

Furthermore, the platform 2, together with the front and rear limb auxiliary supports 3 and 4, is supported on a lift unit 7 which is adjustable in height relative to a weight measurement unit 6. The weight measurement unit 6 has a set of sole electrodes 8 consisting of impedance measurement electrodes 8a, 8b, 8c and 8d provided on an upper surface thereof for making contact with soles of four limbs of the animal. In particular, they are: current applying electrodes 8a and 8b for making contact with the soles of left-hand side front and rear limbs; and voltage measurement electrodes 8c and 8d for making contact with the soles of right-hand side front and rear limbs of the animal.

The weight measurement unit 6 further includes an operation unit 9 for operating the animal body fat measuring device 1 and a display unit 10 for displaying the result of measurement, guidance information, etc. In particular, the operation unit 9 includes a lift adjusting key for adjusting the height of the lift unit 7, a ten-key with direction keys for numerical input and selection, a power switch, a measurement start switch, and the like.

FIG. 2 is a view illustrating the measuring device at the time when the first measuring process is being done to measure the impedance using the set of trunk portion electrodes 5 while fixing the animal therein, and also illustrating the principle of measurement. In particular, the body of the animal under test is placed on the platform 2, and the front limb auxiliary support 3 and the rear limb auxiliary support 4 are drawn to such positions that they become contact to the roots of the front and rear limbs of the animal to support the trunk portion of the animal. Then, the lift adjusting key on the operation unit 9 is operated to rise the height of the lift unit 7 until the four limbs of the animal become floated in the air to reach the animal fixing condition at which the first impedance measurement process is conducted.

The principle of measurement is such that an electric current is passed through the current applying electrodes 5a and 5b which are directly contact to the trunk portion of the animal in the animal fixing condition, as shown, and the impedance is measured between the voltage measurement electrodes 5c and 5d which are mounted at the position inside relative to the current applying electrodes 5a and 5b, respectively.

Then, the platform 2 is lowered automatically or by adjusting the height of the lift unit 7 using the lift adjusting key on the operation unit 9 from the position at which the animal fixing condition is kept, as shown, until the soles of four limbs of the animal supported on the platform 2 become contact to the set of sole electrodes 8, respectively. As the platform 2 is further lowered the platform 2 and the front and the rear limb auxiliary supports 3 and 4 are separated from the trunk portion of the animal, together with the set of trunk portion electrodes 5. As the result, the animal stands on the weight measuring unit 6 with four limbs being contact to the set of sole electrodes 8, respectively, to enter the second impedance measurement process.

In view of transition from the first to the second impedance measurement process, as described above, the weight measurement unit 6 and the set of sole electrodes 8 provided thereon should have at least such size that the soles of four limbs of the animal are sure to land on the sole electrodes 8a, 8b, 8c and 8d, respectively, as the platform 2 is lower from the position at which the animal fixing condition is kept.

Next, the internal components of the animal body fat measuring device 1 will be described in more detail with reference to the electrical block diagram of FIG. 3. The set of trunk portion electrodes 5 and the set of sole electrodes 8 are all connected to a switching unit 20 which also includes a grounding connection. The switching unit 20 is connected to a controller unit 23, together with a current applying unit 21 and a voltage measurement unit 22.

Also connected to the controller unit 23 are: a distance-between-limbs measurement unit 24 for measuring the distance between front and rear limbs that is the body length of the animal supported on the platform by measuring the distance in movement of the drawer portions 3 and 4 with an encoder (not shown); an arithmetic unit 25 for calculating the body fat rate of the animal using the data measured or entered; and a memory unit 26 in which various types of calculation formulae, measurement results, etc. are stored. In addition, the weight measuring unit 6, the lift unit 7, the operation unit 9 and the display unit 10, as described above, are also connected to the controller unit 23, together with a power supply 27.

The switching unit 20 is provided to switch between the set of trunk portion electrodes 5 and the set of sole electrodes 8 so that either one of them is connected to the current applying unit 21 and the voltage measurement unit 22 in order to perform either one of the first and second impedance measurement process. In addition, when the current applying unit 21 and the voltage measurement unit 22 are connected to ground the third process is performed in which the body fat rate is calculated based on the morphological measurement.

More particularly, the connection, as indicated by a solid line in the figure, extending to the set of trunk portion electrodes 5 from the current applying unit 21 and the voltage measurement unit 22 is made for performing the first impedance measurement process. On the other hand, the connection, as indicated by a broken line in the figure, extending to the set of sole electrodes 8 is made for performing the second impedance measurement process. Although not shown in the figure, when the current applying unit 21 and the voltage measurement unit 22 are connected to ground, the resulting connection is made for the third process in which the measurement of impedance is not done, instead the body fat rate is calculated based on the morphological measurement.

Figure 4:
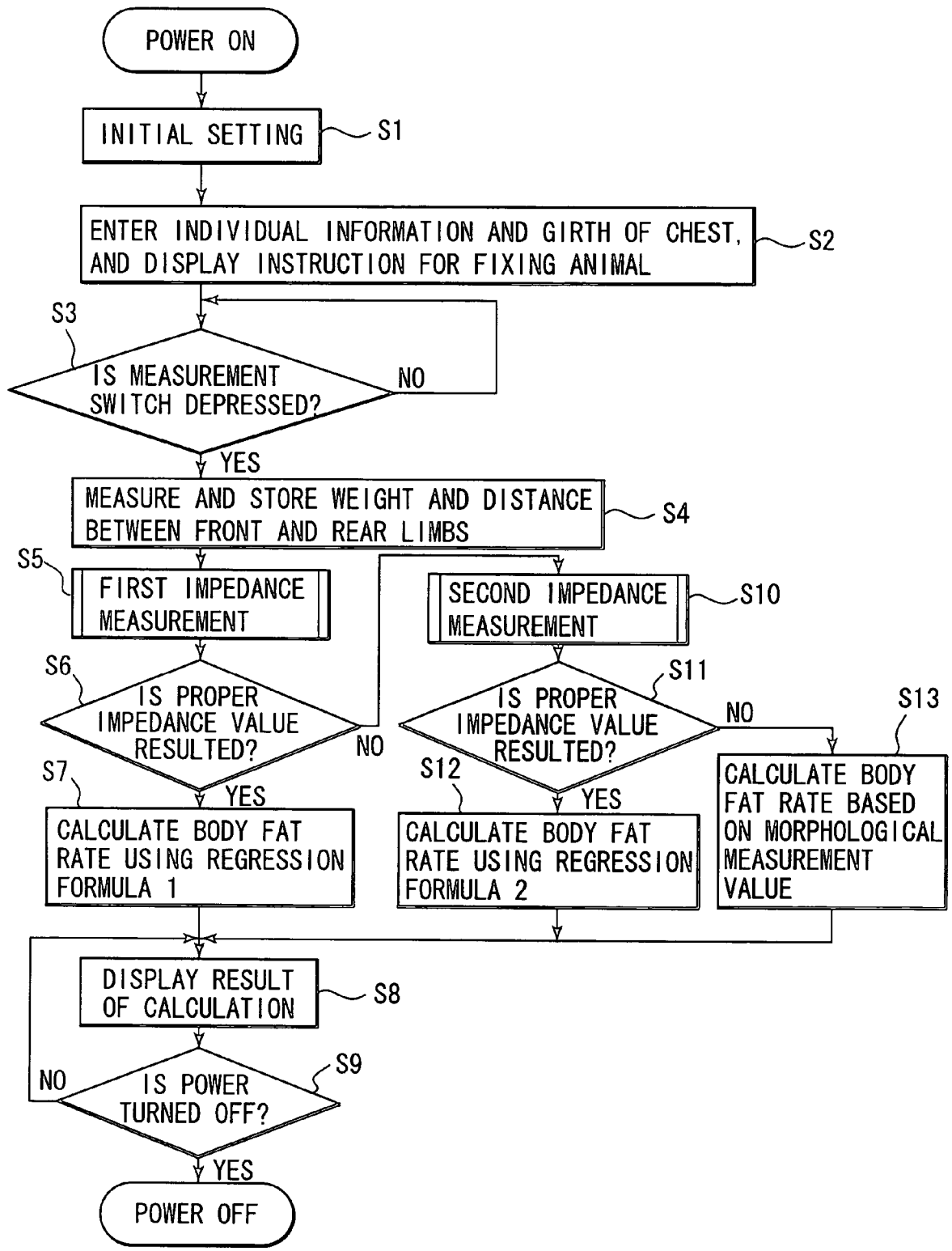
FIG. 4 is a main flow chart illustrating operation of the measuring device.
Figure 5:
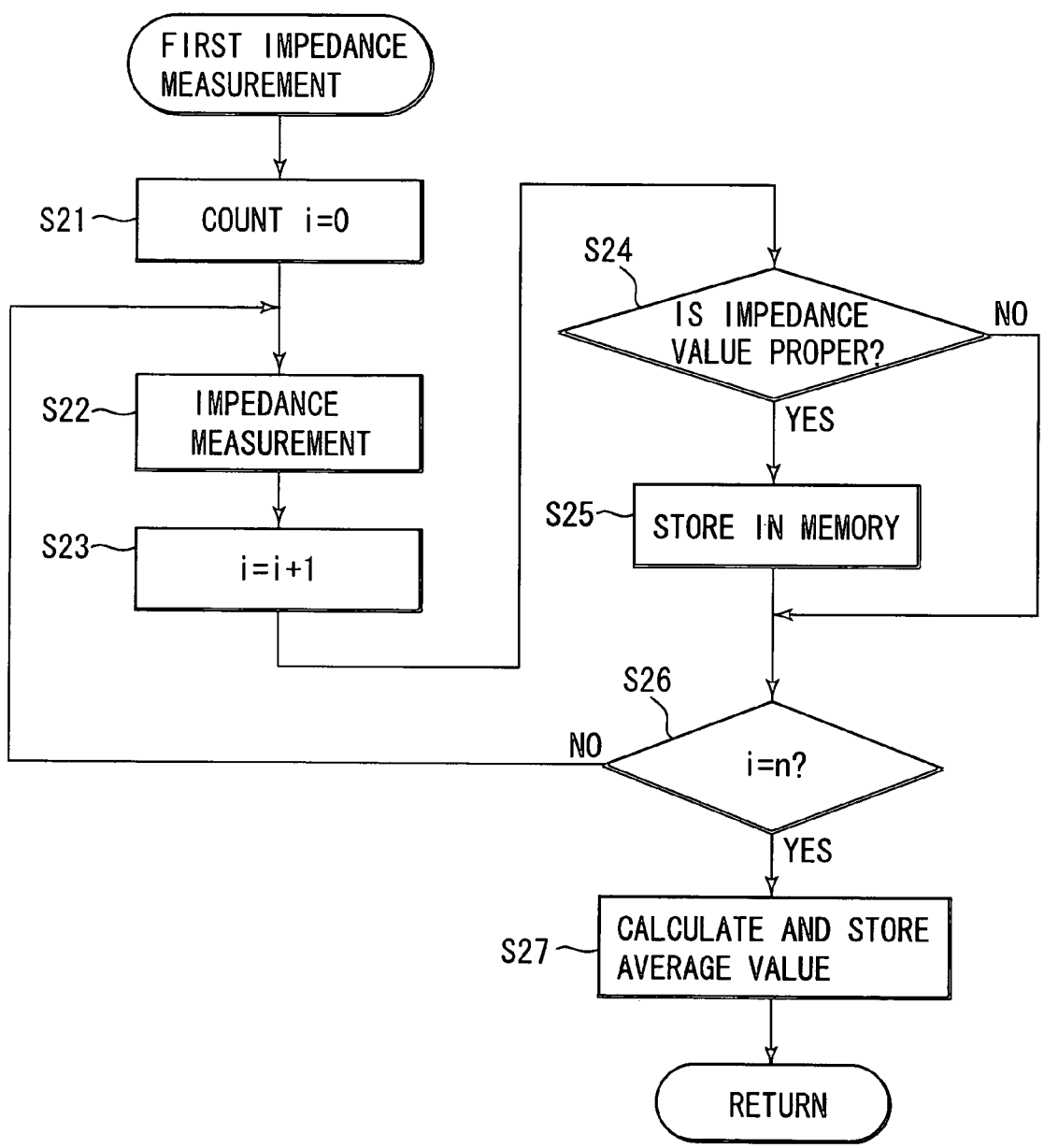
FIG. 5 is a sub-flow chart illustrating the first impedance measurement process.
Figure 6:
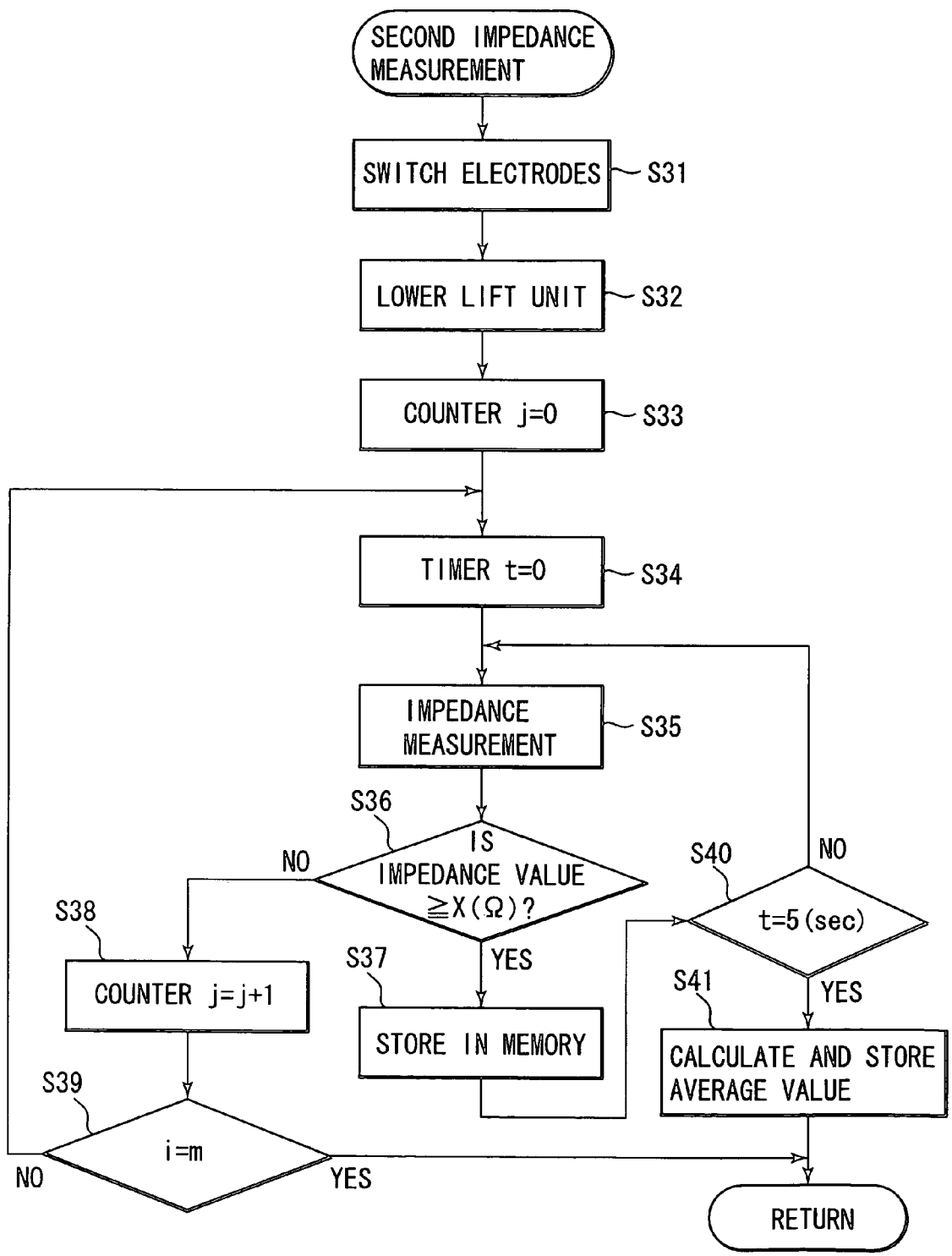
FIG. 6 is a sub-flow chart illustrating the second impedance measurement process.
Figure 7:
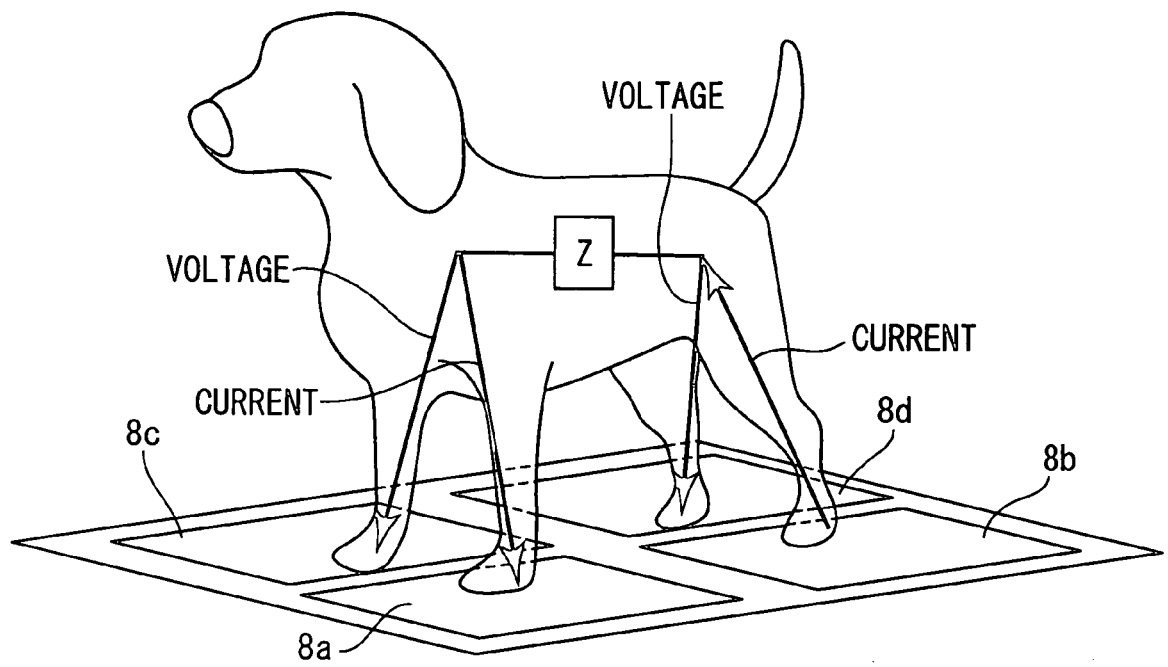
FIG. 7 is a view illustrating the principle of measurement for the second impedance process.

Referring now to FIGS. 4 to 7, operation of the animal body fat measuring device 1 according to the present invention will be described in more detail. In this example, an animal under test of which body fat is to be measured by the device 1 is a dog. In particular, FIG. 4 is a main flow chart; FIG. 5 is a sub-flow chart illustrating the first impedance measurement process using the set of trunk portion electrodes 5; FIG. 6 is a sub-flow chart illustrating the second impedance measurement process using the set of sole electrodes 8; and FIG. 7 is a view illustrating the principle of measurement for the second impedance process.

Referring, first, to the main flow chart of FIG. 4, the power switch on the operation unit 9 is operated to turn ON the body fat measuring device 1. Then, at step S1 an initialization procedure is executed. In this initialization procedure the switching unit 20 is connected to the controller unit 23 and is switched to the position where the impedance measurement is performed using the set of trunk portion electrodes 5. That is to say, the trunk portion electrodes 5a and 5b are connected to the current applying unit 21 and the trunk portion electrodes 5c and 5d are connected to the voltage measurement unit 22.

Then, at step S2 a message is displayed on the display unit 10 for prompting a user to enter the individual information and the girth of chest of the dog and to start the measurement by depressing the measurement switch on the operation unit 9 after the dog is fixed. Next, at step S3 a check is done to determine whether the measurement switch is depressed or not. If not, the routine proceeds to "NO" branch to perform the check again.

In the first embodiment the individual information is defined as consisting of type, sex and age of a dog under test. In particular, the type of the dog may be entered in such manner that a cursor operable using the ten-key with the direction keys on the operation unit 9 and a plurality of types of dogs selectable by the cursor are displayed on the display unit 10 and then any one of those types of dogs is selected by using the cursor for entering. The girth of chest is defined as the girth of the body at the position of the roots of front limbs. For example, the numerical value for the girth of chest provided in advance using some measuring tool may be entered with the ten-key on the operation unit 9.

After the individual information and the girth of chest have been entered, the dog has been fixed as described in connection with FIG. 2, and the measurement switch on the operation unit 9 has been depressed at step S3 then the routine proceeds via "YES" branch of step S3 to step S4. In this step S4 the weight of the dog is measured by the weight measurement unit 6, the distance between front and rear limbs of the dog is automatically measured by the distant-between-limbs measurement unit 24, and each of the data is automatically stored in the memory unit 26. Then, at step S5 the first impedance measurement process using the set of trunk portion electrodes 5 is performed, which will be described hereafter with reference to FIG. 5.

At step S6 a check is made to determine whether the proper impedance value is provided by the first impedance measurement process. In the first impedance measurement process the measurement of impedance is done several times and only the impedance values considered proper are averaged. Accordingly, it is determine, here, whether such average value is stored in the memory unit 26.

If the average value is stored, the routine proceeds via "YES" branch of step S6 to step S7 where a body fat rate calculation formula suitable for the individual information that has been entered is retrieved from the memory unit 26 in which a plurality of body fat rate calculation formulae for the first impedance measurement process are stored for each of the individual information, and then, the body fat rate is calculated in the arithmetic unit 25. Then, at step S8 the result of calculation is displayed on the display unit 10. It is noted, here, that the body fat rate calculation formula for the first impedance measurement process is a regression formula 1 which is resulted from multi-correlation between the body fat rate provided by "DEXA" measurement in advance, the average of impedance provided by the first impedance measurement process, the body weight, the distance between front and rear limbs, and the girth of chest. For example, the formula is written as follows:

Body Fat Rate (% FAT)=α×Averaged Impedance+β× Body Weight+γ×(Girth of Chest/Distance between Front and Rear Limbs)+δ where α, β, γ and δ are constants.

However, if the averaged impedance value is not stored in the memory unit 27 at step S6 then it is determined that no proper impedance value is provided in the first impedance measurement process. Then, the routine proceeds via "NO" branch of step S6 to step S10 where the switching unit 20 is switched under the control of the controller unit 23 to such position that the current applying unit 21 and the voltage measurement unit 22 are connected to the set of sole electrodes 8, instead of the set of trunk portion electrodes 5, in order to transfer to the second impedance measurement process, which will be described hereafter with reference to FIG. 6.

At step S11 a check is made to determine whether the proper impedance value is provided by the second impedance measurement process. In the second impedance measurement process an average of the impedance stably measured within the predetermined time period is calculated. Accordingly, it is determine, here, whether such average value is stored in the memory unit 26.

If the average value is stored, the routine proceeds via "YES" branch of step S11 to step S12 where a body fat rate calculation formula suitable for the individual information that has been entered is retrieved from the memory unit 26 in which a plurality of body fat rate calculation formulae for the second impedance measurement process are stored for each of the individual information, and then, the body fat rate is calculated in the arithmetic unit 25. Then, at step S8 the result of calculation is displayed on the display unit 10. It is noted, here, that the body fat rate calculation formula for the second impedance measurement process is a regression formula 2 which is resulted from multi-correlation between the body fat rate provided by "DEXA" measurement in advance, the average of impedance provided by the second impedance measurement process, the body weight, the distance between front and rear limbs, and the girth of chest. For example, the formula is written as follows:

Body Fat Rate (% FAT)=ϵ×Averaged Impedance+ζ× Body Weight+η×(Girth of Chest/Distance between Front and Rear Limbs)+θ where $\epsilon$, $\zeta$, $\eta$ and $\theta$ are constants.

However, if the averaged impedance value is not stored in the memory unit 27 at step S11, that is to say, if it is determined that no proper impedance value is provided in the second impedance measurement process, in addition to the first impedance measurement process, then the routine proceeds via "NO" branch of step S11 to step S13 where the body fat rate is calculated based on the morphological measurement value.

At step S13 the switching unit 20 is switched under the control of the controller unit 23 to such position that the current applying unit 21 and the voltage measurement unit 22 are connected to ground so that the power to the set of trunk portion electrodes 5 and the set of sole electrodes 8 is interrupted. Then, the body fat rate calculation formula for the morphological measurement is retrieved from the memory unit 26 and the body fat rate is calculated in the arithmetic unit 25. Thereafter, the result of calculation is displayed on the display unit 10. The body fat rate calculation formula for the morphological measurement is a regression formula 3 which is resulted from multi-correlation between the body fat rate provided by "DEXA" measurement in advance, the girth of chest, the distance between front and rear limbs, and the body weight. For example, the formula is written as follows:

Body Fat Rate (% FAT)=κ×Body Weight+λ×(Girth of Chest/Distance between Front and Rear Limbs)+μ where $\kappa$, $\lambda$, and $\mu$ are constants.

Then, at step S9 a check is made to determine whether the power switch on the operation unit 9 is depressed. If it is not depressed the routine proceeds via "NO" branch of step S9 to step S8. Then, step S8 and S9 are executed again. However, if the power switch is depressed then the routine proceeds to "YES" branch of the step S9 so that the power to the device is turned OFF to terminate the measurement.

Now, the first impedance measurement process at step S5 in FIG. 4 will be described in more detail with reference to FIG. 5.

The first impedance measurement process is executed in such manner that at step S21 an impedance measurement counter in the controller unit 23 is initially set to i=0. Then, at step S22 the impedance measurement using the set of trunk portion electrodes 5 is performed on the basis of the principle of measurement that has been described with reference to FIG. 2. Thereafter, at step S23 the counter is incremented by one (i=i+1) and at step S24 a check is made to determine whether the measured impedance value is proper or not.

The determination for the impedance value, as above, is performed by calculating the resistivity based on the impedance value. In particular, assuming that the measured impedance value is "Z", the distance between front and rear limbs and the girth of chest in the main routine of FIG. 4 are "L" and "C", respectively, and the trunk portion of the dog is modeled by a cylinder having length "L" and circumference "C", then the volume of the cylinder is written by the following formula:

$$V=(C/2\pi)^2 \times L \times \pi$$

Furthermore, the resistivity "ρ" is written by the following formula:

$$\rho=V \times Z/L^2$$

Accordingly, the resistivity "ρ" of the trunk portion of the dog is written by the following formula:

$$\rho=(C/2\pi)^2 \times \pi \times Z/L$$

On the other hand, if it is considered that the living body consists of three living body elements: muscle; fat; and bone, then the resistivity of each living body element is generally defined as follows:
Resistivity of muscle ρm=250 (Ω·cm);
Resistivity of fat ρf=2500 (Ω·cm); and
Resistivity of bone ρb=1750 (Ω·cm).
Accordingly, the judgment criterion is such that if the resistivity "ρ" is within the range (hereafter referred to as "proper range") of $250 \leq \rho \leq 2500$ then the living body element is determined as having been correctly measured and the measured impedance value "Z" is considered proper.

Therefore, the resistivity "ρ" is calculated in the arithmetic unit 25 and is compared with the proper range for the resistivity stored in the memory unit 26 in advance to determine whether the measured impedance value is proper or not.

If it is determined that the measured impedance value is proper then the routine proceeds via "YES" branch of step S24 to step S25 where the measured impedance value is stored in the memory unit 26. Thereafter, the routine proceeds to step S26. However, if the measured impedance value is not proper in step S24 then the routine proceeds via "NO" branch of step S24 to step S26 without any storage of the measured impedance value in the memory unit 26. As the result, the memory unit 26 stores only the impedance values that have been determined proper.

At step S26 a check is done to determine whether the count "i" reaches the preset number of times "n" or not. If it does not reach "n", the routine proceeds to step S22 where the measurement of impedance is performed again. However, if it reaches "n" the routine proceeds to step S27 where the average of the impedance values stored in the memory unit 26 is calculated and then it is stored again in the memory unit 26. Thereafter, the routine returns to the main flow chart in FIG. 4.

Now, the second impedance measurement process at step S10 in FIG. 4 will be described in more detail with reference to FIGS. 6 and 7.

The second impedance measurement process is performed in such manner that at step S31 the switching unit 20 is operated under the control of the controller unit 23 so that the set of electrodes used is switched from the set of trunk portion electrodes 5 to the set of sole electrodes 8. In particular, although the current applying unit 21 has been connected to the trunk portion electrodes 5a and 5b in the first impedance measurement process it is now switched to connect to the sole electrodes 8a and 8b. In the same manner, although the voltage measurement unit 22 has been connected to the trunk portion electrodes 5c and 5d in the first impedance measurement process it is now switched to connect to the sole electrodes 8c and 8d.

Then, at step S32 the lift unit 7 is operated under the control of the controller unit 23 to automatically lower in height so that the platform 2, the front and rear limb auxiliary supports 3 and 4, and the set of trunk portion electrodes 5 are separated from the trunk portion of the dog. Although the body fat measuring device 1 is not shown with such condition, the soles of four limbs of the dog are contact with the set of sole electrodes 8, respectively, as can be seen in FIG. 7 illustrating the principle of measurement. When the lift 7 reaches the lower limit, at step S33, a number-of-times counter in the controller unit 23 is set to "j=0", and at step S34, a timer is set to "t=0". Then, the timer is started concurrently with the start of impedance measurement. The number-of-times counter has the upper limit setting of "j=m" and is incremented every time when the measured impedance value is determined improper. The timer has an impedance measurement time setting of "t=5 sec".

At step S35 the impedance of trunk portion of the dog is derived by impedance measurement according to prior art four-electrode method. In particular, as shown in FIG. 7 illustrating the principle of measurement, an electric current is passed through the left-hand front and rear soles and the trunk portion of the dog, and the voltage is measured across the right-hand front and rear soles. Accordingly, it is possible to measure the impedance of the trunk portion, as indicated by "Z" in the figure, without having any effect of four limbs of the dog.

After measurement of the impedance, at step S36, a check is made to determine whether each of soles of the dog is contact with each of the sole electrodes 8. That is to say, if the measured impedance value is not less than the experimentally determined threshold of $X(\Omega)$ then each of soles of the dog is considered contact with each of the sole electrodes 8. Then, the routine proceeds via "YES" branch of step S36 to step S37 where the measured impedance value is stored in the memory unit 26. Then, at step S40 a check is done to determine whether the timer reaches "t=5 (sec)" or not. If the answer is "NO", the routine returns to step S35 where the measurement of impedance is started again. However, if the answer is "YES", the routine proceeds to step S41 where the average of the impedance values stored in the memory unit 26 is calculated and it is stored in the memory unit 26 again. Then, the routine returns to the main flow chart of FIG. 4.

If the measured impedance value is less than $X(\Omega)$ in step S36, that is to say, if any of the soles of the dog is not contact with the sole electrodes 8 then the routine proceeds via "NO" branch of step S36 to step S38 where the counter is incremented by one (j=j+1) and the data of impedance value stored in the memory unit 26 for this second impedance measurement process is deleted. Then, at step S39 a check is made to determine whether the counter reaches the upper limit of j=m. If the answer is "NO" the routine return to step S34 where the timer is set to "t=0" again and the measurement of impedance is started again. However, if the answer is "YES" the routine returns to the main flow chart of FIG. 4.

In the second impedance measurement process, as described above, the impedance value can be get only if the measurement of impedance could stably be done for a period of t=5 (sec).

As described above, at step S3, the girth of chest that has been measured with some measuring tool in advance is numerically entered through the operation unit 9. However, the present invention is not limited to such configuration. For example, a measuring tool with an automatic distance measuring encoder may be included in the front limb auxiliary supports 3, and after the animal is fixed, the measuring tool with the encoder may be extended from the front limb auxiliary supports 3 to wrap around the chest portion of the animal, thereby automatically measuring the girth of chest portion, which is then stored in the memory unit 26.

The girth of chest is defined as the girth of body measured at the position of roots of front limbs. However, the girth of body at any position within the range of trunk portion of the animal may be used so far as the specific position is determined as the place where the measurement is always done, including regression formula.

As described above, in the first impedance measurement process the animal is fixed in position in such manner that the animal lies on one's belly on the platform 2 and the front and rear limb auxiliary supports 3 and 4 while floating the four limbs of the animal in the air. Furthermore, a fixing belt may additionally be provided on at least one of the platform 2 and the front and rear limb auxiliary supports 3, 4 at the side wall thereof. The corresponding lock member for locking the fixing belt may also be provided at opposite side wall. Then, during the time the animal is fixed the fixing belt is run to wrap around the back of the animal and is locked by the lock member to reliably catch and hold the animal in position.

As also described above, in the second impedance measurement process the animal is measured in such condition that the soles of four limbs of the animal are contact with the sole electrodes 8a, 8b, 8c and 8d, respectively. Furthermore, some additional auxiliary tool may be provided for preventing the sole of the animal from contacting with other sole electrode than its associated sole electrode. For example, a partition board may be provided between adjacent electrodes in order not to move the limb of the animal to other electrode. Alternatively, a hollow cylinder movable only in an area of each electrode may be provided so that each limb of the animal is inserted into each cylinder to make sure that each sole of the animal is contact with its associated electrode.

In the embodiment, as described above, a dog is described as being an animal under test. However, even for other animals each having four limbs the present invention is similarly applicable to derive the body fat rate of the animal in such manner that the switching is made between the first impedance measurement, the second impedance measurement, and the calculation of body fat based on morphological measurement, depending on which one is suitable, and that the body fat calculation formulae for the first and second impedance measurement and the morphological measurement are stored in the memory unit 26 for each of animals. For example, in case where measurement of a horse is performed the first impedance measurement process is considered suitable. Because of hooves of the soles of the horse the second impedance measurement process can't be performed. Even if the first impedance measurement can't be performed due to any effect of body hair it is still possible to perform the calculation of body fat based on morphological measurement. In such case the measuring device of the present invention may be configured to have no set of sole electrodes 8 provided therein for the second impedance measurement process. In such manner it is generally possible to provide at least one of the set of trunk portion electrodes 5 and the set of sole electrodes 8 to suit the animal under test.

Description of Second Embodiments

A body fat measuring device according to a second embodiment of the present invention is configured in such manner that if a person under test who is a child can't behave to rest for a fixed time period or may move apart from the electrodes, or if there is less possibility to conduct stable impedance measurement, then switching is made to enter such mode that calculation of body fat rate is performed based on morphological measurement.

Figure 8:
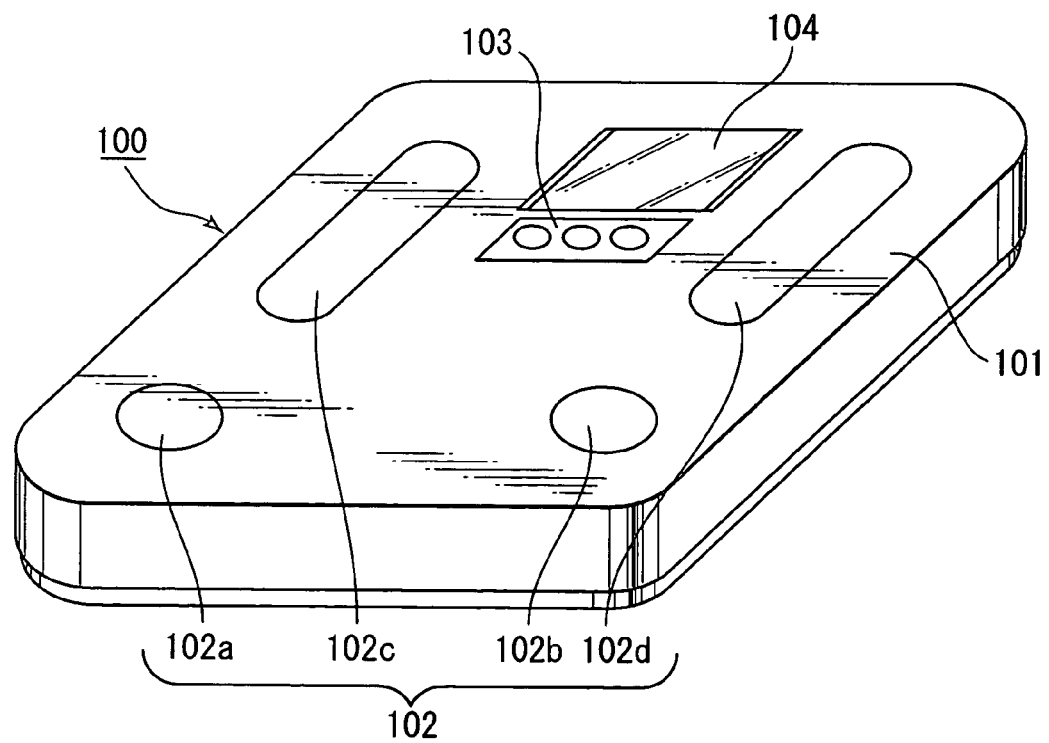
FIG. 8 is an external view of the body fat measuring device according to the second embodiment.
Figure 9:
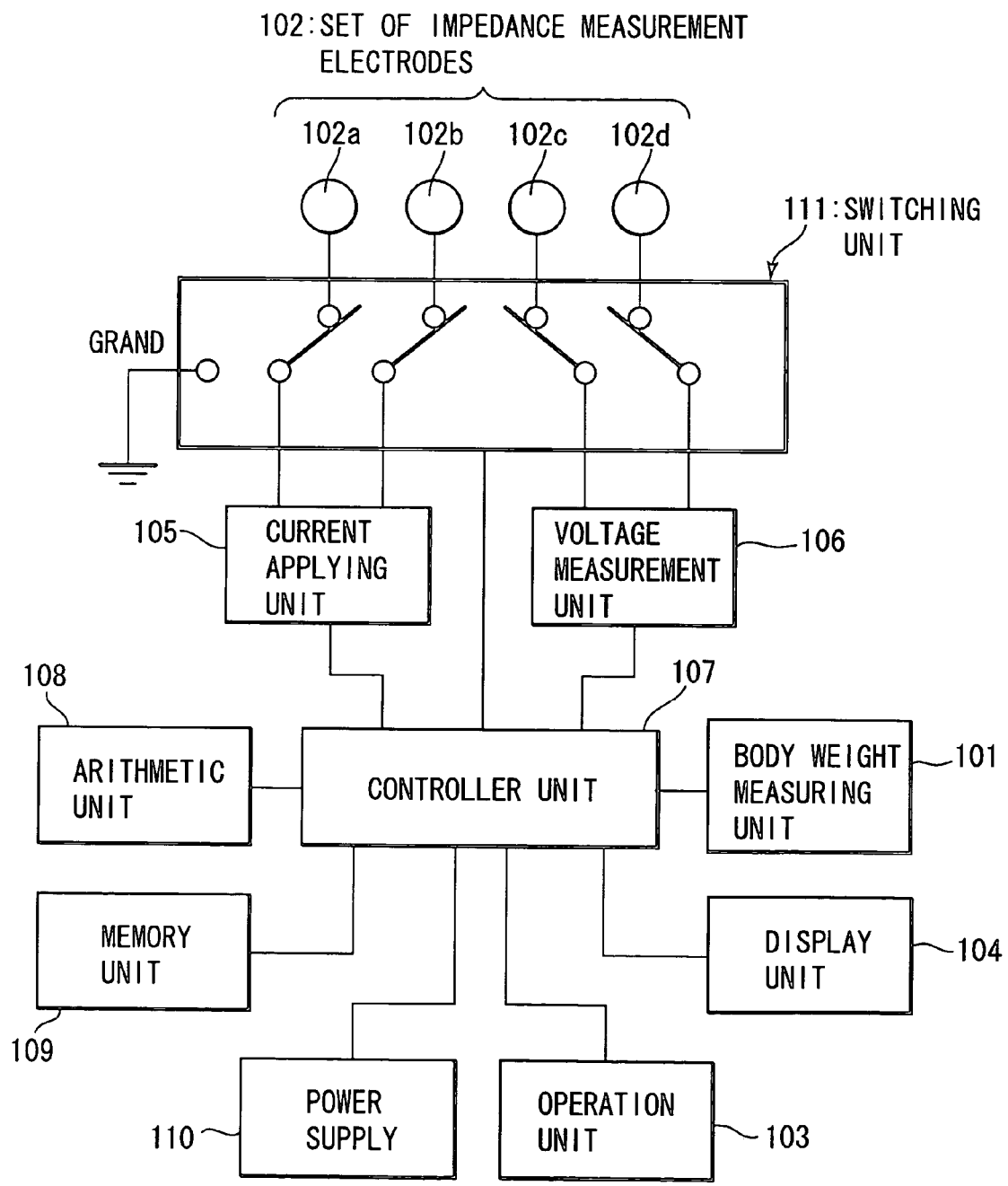
FIG. 9 is an electrical block diagram of the measuring device according to the second embodiment.
Figure 10:
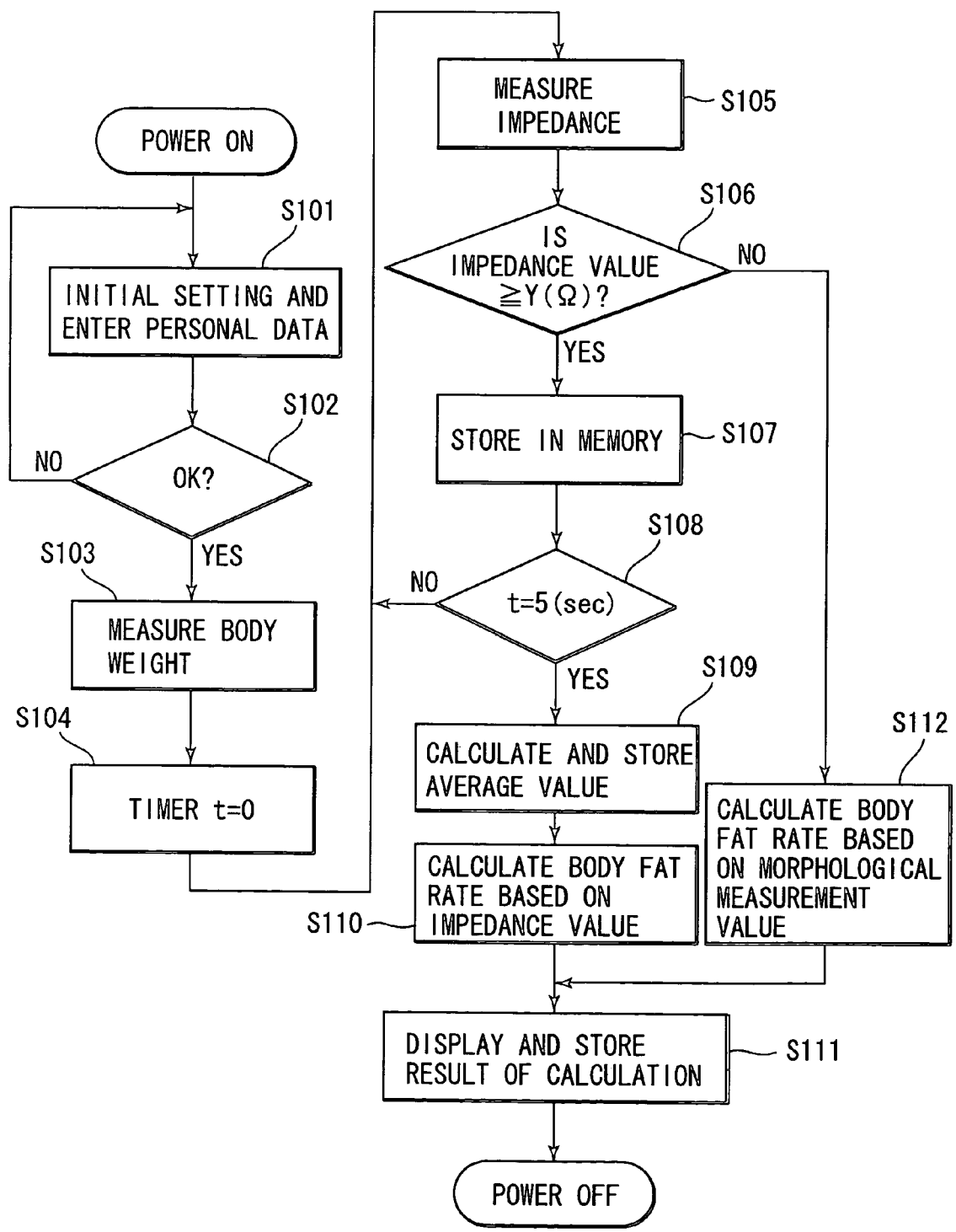
FIG. 10 is a flow chart illustrating operation of the measuring device according to the second embodiment.

Now, the body fat measuring device according to the second embodiment will be described in more detail with reference to FIGS. 8 to 10. In particular, FIG. 8 is an external view of the body fat measuring device according to the second embodiment; FIG. 9 is an electrical block diagram of the measuring device; and FIG. 10 is a flow chart illustrating operation of the measuring device.

The body fat measuring device 100 in FIG. 8 has the same external appearance as that of a common body fat measuring apparatus in the prior art. In particular, the device 100 includes a body weight measuring platform 101 and a set of impedance measurement electrodes 102 provided on the platform 101. The set of electrodes 102 consists of current applying electrodes 102a and 102b as well as voltage measurement electrodes 102c and 102d. An operation unit 103 and a display unit 104 are also provided on the platform 101.

Next, internal components in the measuring device 100 will be described in more detail with reference to the electrical block diagram of FIG. 9. The set of impedance measurement electrodes 102 is connected to a switching unit 111 having a grounding connection. The switching unit 111 is connected to a current applying unit 105 and a voltage measurement unit 106. Furthermore, the switching unit 111, the current applying unit 105 and the voltage measurement unit 106 are all connected to a controller unit 107.

The switching unit 111 is provided to switch between the set of impedance measurement electrodes 102 and the ground point so that the current applying unit 105 and the voltage measurement unit 106 are connected to either one of them.

Also connected to the controller unit 107 are: an arithmetic unit 108 for calculating the body fat rate using the impedance value or morphological measurement value; and a memory unit 109 for storing the body fat rate calculation formulae and the result of measurement.

In addition, the weight measuring unit 101, the operation unit 103 and the display unit 104, as described above, are also connected to the controller unit 107, together with a power supply 110.

Now, operation of the body fat measuring device 100 according to the second embodiment will be described in more detail with reference to FIG. 10. First of all, the operation unit 103 is operated to turn ON the power supply of the device. Then, at step S101 an initial setting is performed and a message is displayed on the display unit 104 for prompting a person under test to enter the personal data such as sex, age, girth of chest and height of the person. It is preferable that the girth of chest and the height are measured in advance, and are entered according to the instruction by the message.

In the initial setting the switching unit 111 is switched under the control of the controller unit 107 to such position that the current applying unit 105 and the voltage measurement unit 106 are connected to the set of impedance measurement electrodes 102. In particular, the current applying unit 105 is connected to the current applying electrodes 102a and 102b, and the voltage measurement unit 106 is connected to the voltage measurement electrodes 102c and 102d.

Then, at step S102 confirmation of the data items is performed, and if it is desired to correct some data item, the operation unit 103 is used to operate a cursor on the display unit 104 for selecting and correcting that data item. However, if there is no data item to be corrected then a measurement start switch on the operation unit 103 is depressed to start the measurement.

Next, at step S103, in response to start of the measurement, the person under test mounts on the body fat measuring device 100 to measure the body weight, which is stored in the memory unit 109. At step S104 a timer provided in the controller 107 for setting the time period of impedance measurement is set to "t=0 (sec)". At step S105 the timer is started concurrently with the start of impedance measurement. At step S106 a check is made to determine whether the measurement of impedance has stably been done, or whether the soles of the person under test have been kept contact with the set of impedance measurement electrodes 102.

That is to say, if the measured impedance value is not less than the experimentally determined threshold of Y($\Omega$) then each of soles of the person is considered contact with each of the set of impedance measurement electrodes 102. Then, the routine proceeds via "YES" branch of step S106 to step S107 where the measured impedance value is stored in the memory unit 109. Then, at step 108 a check is made to determine whether the timer reaches "t=5 (sec)". If it does not reach the routine proceeds via "NO" branch of step S108 to step S105 where the measurement of impedance is started again.

However, if the timer reaches "t=5 (sec)" the routine proceeds via "YES" branch of step S108 to step S109 where an average for impedance values stored in the memory unit 109 is calculated in the arithmetic unit 108 and it is stored in the memory unit 109. Then, at step S110 the body fat rate is calculated using the well known regression formula retrieved from the memory 109 for calculating the body fat rate based on sex, age, height, body weight and impedance value. Thereafter, at step S11l the result of measurement is displayed on the display unit 104 and is stored in the memory unit 109.

If the measurement impedance value is less than the threshold at step S106 then it is considered that the soles of the person under test is separated from any of the set of impedance measurement electrodes 102. The routine proceeds via "NO" branch of the step S106 to step S112 where the switching unit 111 is switched under the control of the controller unit 107 to such position that the current applying unit 105 and the voltage measurement unit 106 are connected to ground, thereby entering the mode wherein the body fat rate is calculated based on morphological measurement value. In particular, the regression formula which is resulted from correlation between sex, age, height, body weight and girth of chest of the person, and the body fat rate provided by "DEXA" measurement in advance is retrieved from the memory unit 109 for calculating the body fat rate. For example, the regression formula is written as follows:

Body Fat Rate(%)=$\nu$Sex+$\xi\times$Age+$\tau\times$(Girth of Chest/Height)+$\upsilon\times$Body Weight+$\phi$ where $\nu$, $\xi$, $\tau$, $\upsilon$ and $\phi$ are constant.

Finally, at step S111 the result of calculation is displayed and stored, and after confirmation, the power switch on the operation unit 103 is turned OFF to terminate the measurement.

What is claimed is:

1. A body fat measuring device for measuring body fat of an animal, comprising:
   an individual information input unit;
   a bioelectric impedance input unit;
   a morphological measurement value input unit;
   an impedance-based calculation unit;

a morphological measurement value-based calculation unit; and a calculation switching unit, wherein said individual information input unit enters individual information of the animal, said bioelectric impedance input unit measures and enters a bioelectric impedance of the animal, said morphological measurement value input unit enters morphological measurement values for the girth of the body of the animal and the length of the body of the animal, said impedance-based calculation unit calculates a body fat rate based on the bioelectric impedance, said morphological measurement value-based calculation unit calculates a body fat rate based on the morphological measurement values for the girth of the body of the animal and the length of the body of the animal, and said calculation switching unit checks to determine whether the resulting bioelectric impedance has been correctly measured or not and then automatically switches between said impedance-based calculation unit and said morphological measurement value-based calculation unit depending on the result of the determination, wherein the calculation switching unit switches between said impedance-based calculation unit and said morphological measurement value-based calculation unit in order of the precision of each calculation unit in body fat rate calculation;

the device further comprising a base, a platform, disposed on the base, for positioning the animal on its belly while the four limbs of the animal float in the air, and a front limb auxiliary support and a rear limb auxiliary support both of which are for drawing from the platform to contact the roots of the front and rear limbs of the animal for supporting the trunk portion of the animal, said bioelectric impedance input unit includes a set of trunk portion electrodes provided at one end portion of the front limb auxiliary support and one end portion of the rear limb auxiliary support for making contact with the trunk portion of the animal, and a set of sole electrodes provided on the base for making contact with the soles of the four limbs of the animal, and the device further comprises a switching unit which acts to automatically switch between the set of trunk portion electrodes and the set of sole electrodes.

2. A body fat measuring device according to claim 1 in which the platform is supported on a height-adjustable lift unit provided on the base.

3. A body fat measuring device according to claim 1 or 2 in which said morphological measurement value input unit includes an operation unit provided on the base.

4. A body fat measuring device according to claim 1 or 2 in which said morphological measurement value input unit includes a distance-between-limbs measurement unit which measures the distance between the front and rear limbs of the animal, based on a distance over which the front limb auxiliary support and the rear limb auxiliary support are moved relative to the platform.

5. A body fat measuring device according to claim 1 or 2 in which said morphological measurement value input unit includes a weight measuring unit provided on the base.

6. A body fat measuring device according to claim 1 or 2 in which said morphological measurement value input unit includes a measuring tool with an automatic distance measuring encoder included in the front limb auxiliary support for measuring the girth of the animal.

* * * * *